(12) United States Patent
Wang et al.

(10) Patent No.: US 12,246,314 B2
(45) Date of Patent: Mar. 11, 2025

(54) DEVICE AND METHOD FOR PURIFYING ORGANIC AMINE SOLUTION

(71) Applicant: HUANENG CLEAN ENERGY RESEARCH INSTITUTE, Beijing (CN)

(72) Inventors: Jinyi Wang, Beijing (CN); Shiwang Gao, Beijing (CN); Lianbo Liu, Beijing (CN); Hongwei Niu, Beijing (CN); Dongfang Guo, Beijing (CN); Shiqing Wang, Beijing (CN)

(73) Assignee: HUANENG CLEAN ENERGY RESEARCH INSTITUTE, Beijing (CN)

( * ) Notice: Subject to any disclaimer, the term of this patent is extended or adjusted under 35 U.S.C. 154(b) by 717 days.

(21) Appl. No.: 17/488,693

(22) Filed: Sep. 29, 2021

(65) Prior Publication Data

US 2022/0016616 A1    Jan. 20, 2022

Related U.S. Application Data

(63) Continuation of application No. PCT/CN2020/115961, filed on Sep. 17, 2020.

(51) Int. Cl.
*B01J 49/60* (2017.01)
*B01J 41/04* (2017.01)
*B01J 47/02* (2017.01)
*C07C 213/10* (2006.01)

(52) U.S. Cl.
CPC .............. *B01J 49/60* (2017.01); *B01J 41/04* (2013.01); *B01J 47/02* (2013.01); *C07C 213/10* (2013.01)

(58) Field of Classification Search
CPC ... B01J 41/00; B01J 41/04; B01J 47/00; B01J 47/02; B01J 47/04; B01J 49/00; B01J 49/05; B01J 49/06; B01J 49/07; B01J 49/09; B01J 49/60; C07C 213/00; C07C 213/10
See application file for complete search history.

(56) References Cited

PUBLICATIONS

Ramer et al., Attenuated Total Reflection Fourier Transform Infrared Spectroscopy, 2013, Encyclopedia of Analytical Chemistry, pp. 1-27 (Year: 2013).*
CN 205019965 U and machine translation, Zhang, 2016 (Year: 2016).*
JP 2011161303 U and machine translation, Kawaguchi et al., 2011 (Year: 2011).*
WIPO, International Search Report for International Application No. PCT/CN2020/115961, Dec. 23, 2020.

* cited by examiner

*Primary Examiner* — Natasha E Young
(74) *Attorney, Agent, or Firm* — Hodgson Russ LLP

(57) ABSTRACT

Provided are a device and a method for purifying an organic amine solution. The device includes an ion exchange bed having an upper feeding port, through which the ion exchange bed is communicated with an inert gas cylinder, a fifth liquid storage tank and a second liquid adding pump; a lower feeding port, through which the ion exchange bed is communicated with a first liquid adding pump; a lower discharging port, through which the ion exchange bed is communicated with a second liquid storage tank, a third liquid storage tank and a fourth liquid storage tank; and an upper discharging port, through which the ion exchange bed is communicated with the fourth liquid storage tank.

12 Claims, 1 Drawing Sheet

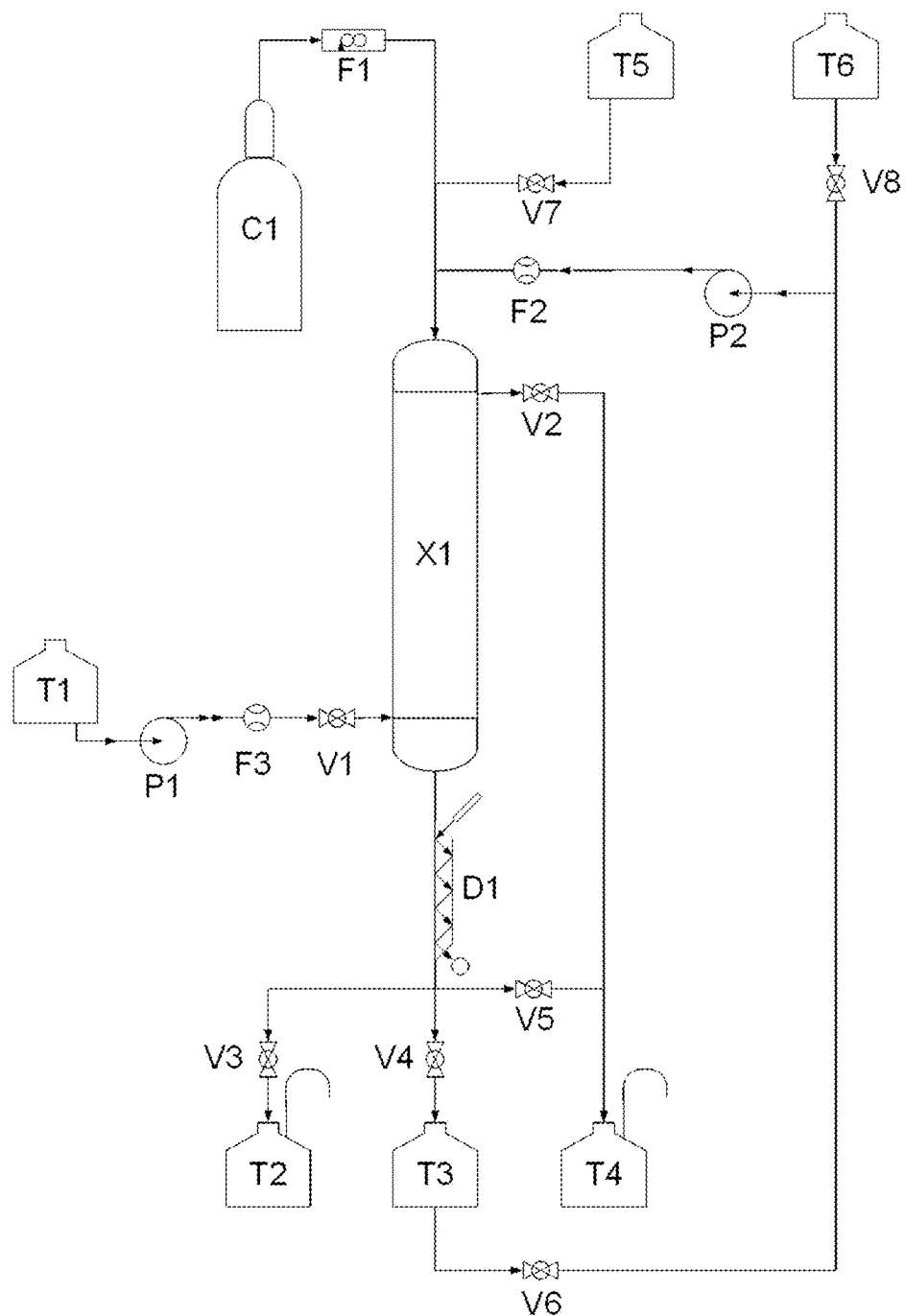

DEVICE AND METHOD FOR PURIFYING ORGANIC AMINE SOLUTION

CROSS-REFERENCE TO RELATED APPLICATIONS

This application is a continuation of the International Patent Application No. PCT/CN2020/115961, now WO 2021/052432, filed Sep. 17, 2020, which claims priority to and benefits of Chinese Patent Application No. 201910889282.8, filed on Sep. 19, 2019, the entire contents of which are incorporated by reference herein.

FIELD

The present disclosure relates to a field of purifying devices, and more particularly to a device and a method for purifying an organic amine solution.

BACKGROUND

In petrochemical and environmental protection industries, an organic amine solution is purified by a chemical absorption method with organic amine absorbents. However, impurities in the raw material may be involved, causing deterioration of the organic amine solution. An amount of effective components in the solution may be decreased, and waste liquid may cause environmental problems.

An existing purification device may include an ion exchange bed having the ion exchange resin. Due to problems such as adhesion and adsorption of the resin to the solution, an excessive dead volume of the device and pipeline, and an inappropriate inlet ratio and residence time, a part of the solution may remain in the ion exchange bed or the pipeline, which cannot be returned to the solution system, and thus causes consumption. In addition, a control program for the existing purification devices is not flexible and thus cannot be adjusted according to a concentration of the solution and an operation state of the purification device.

SUMMARY

An object of the present disclosure is to provide a device and a method for purifying an organic amine solution.

In embodiments of a first aspect of the present disclosure, a device for purifying an organic amine solution is provided, the device has a low amine loss and includes an ion exchange bed. The ion exchange bed has an upper feeding port, through which the ion exchange bed is communicated with an inert gas cylinder, a fifth liquid storage tank and a second liquid adding pump by pipelines, a first flow meter is provided on an outlet pipeline of the inert gas cylinder, and a seventh valve is provided on a discharging pipeline of the fifth liquid storage tank. The ion exchange bed has a lower feeding port, through which the ion exchange bed is communicated with a first liquid adding pump by a pipeline, and the first liquid adding pump has an extraction port, through which the first liquid adding pump is communicated with a first liquid storage tank by a pipeline. The ion exchange bed has a lower discharging port, through which the ion exchange bed is communicated with a second liquid storage tank, a third liquid storage tank and a fourth liquid storage tank by pipelines, a multiple total reflection infrared spectrum analyzer is provided on a discharging pipeline from a lower end of the ion exchange bed, a third valve is provided on a feeding pipeline of the second liquid storage tank, a fourth valve is provided on a feeding pipeline of the third liquid storage tank, and a fifth valve is provided on a pipeline communicating the fourth liquid storage tank with the ion exchange bed through the lower discharging port. The ion exchange bed has an upper discharging port, through which the ion exchange bed is communicated with the fourth liquid storage tank by a pipeline, and a second valve is provided on a pipeline communicating the fourth liquid storage tank with the ion exchange bed through the upper discharging port.

In an embodiment, a second flow meter is provided on a discharging pipeline of the second liquid adding pump, and the second liquid adding pump has an extraction port, through which the second liquid adding pump is communicated with a third liquid storage tank and a sixth liquid storage tank by pipelines.

In an embodiment, a sixth valve is provided on a discharging pipeline of the third liquid storage tank, and an eighth valve is provided on a discharging pipeline of the sixth liquid storage tank.

In an embodiment, a third flow meter and a first valve are provided on a discharging pipeline of the first liquid adding pump.

In an embodiment, the first liquid storage tank is a raw liquid tank, the second liquid storage tank is a waste liquid tank, the third liquid storage tank is a recycled lye tank, the fourth liquid storage tank is a purified liquid tank, and the fifth liquid storage tank is a deionized water tank.

In an embodiment, the sixth liquid storage tank is a purified lye tank.

In an embodiment, a gas discharge port is provided at a top of the second liquid storage tank and a top of the fourth liquid storage tank, respectively.

In embodiments of a second aspect of the present disclosure, a method for purifying an organic amine solution is provided. The method is applied by the device as described in the first aspect and includes:

1): purifying: placing the organic amine solution to be purified in the first liquid storage tank, starting a cycle, opening the first liquid adding pump, the first valve and the second valve, feeding the amine solution into the ion exchange bed from a bottom of the ion exchange bed, purifying the amine solution, transporting a purified solution to the fourth liquid storage tank from a top of the ion exchange bed, and restoring the device to an initial state after the purifying is performed for a period of time;

2): purging with an inert gas: opening the inert gas cylinder, the first flow meter and the fifth valve, introducing the inert gas into the ion exchange bed from the top of the ion exchange bed to discharge the amine solution remaining in the ion exchange bed into the fourth liquid storage tank, and restoring the device to the initial state;

3): washing with water: opening the seventh valve to add deionized water contained in a fifth liquid storage tank to the ion exchange bed from the top of the ion exchange bed, closing the seventh valve until a preset liquid level is reached, and opening the third valve to discharge a waste liquid to the second liquid storage tank after the ion exchange resin in the ion exchange bed is soaked with the deionized water for a preset period of time;

4): purging with the inert gas: opening the inert gas cylinder and the first flow meter, opening a third valve or the fifth valve according to a detected result of the multiple total reflection infrared spectrum analyzer, introducing the inert gas from the top of the ion exchange bed to discharge the waste liquid remaining in the ion exchange bed, if an amine concentration of the waste liquid in a previous step is lower than a preset value, opening the third valve to discharge the waste liquid into the second liquid storage tank, otherwise, opening the fifth valve V5 to discharge the waste liquid into the liquid storage tank T4;

5): pre-regenerating: opening the second liquid adding pump P2, the sixth valve V6 and the third valve V3, adding a recycled lye contained in the third liquid storage tank T3 to the ion exchange bed X1 from the top of the ion exchange bed X1, rinsing the ion exchange resin from top to bottom for pre-regenerating, transporting the generated liquid into the second liquid storage tank T2, and restoring the device to the initial state;

6): regenerating: opening the second liquid adding pump, the eighth valve and the fourth valve, adding a lye contained in the sixth liquid storage tank to the ion exchange bed from the top of the ion exchange bed by the second liquid adding pump, and washing and removing impurity ions adsorbed on the resin surface from top to bottom to regenerate the resin, collecting the washed waste liquid to the third liquid storage tank as the recycled lye, and restoring the device to the initial state;

7): purging with the inert gas: opening the inert gas cylinder, the first flow meter F1 and the third valve to discharge the lye remaining in the ion exchange bed into the second liquid storage tank, and restoring the device to the initial state; and 8): completing the cycle and starting a next cycle.

In an embodiment, in the washing 3), if the amine concentration of the waste liquid detected by the multiple total reflection infrared spectrum analyzer is higher than the preset value, the third valve is closed and the fifth valve is opened to allow the waste liquid with a high amine concentration flow into the fourth liquid storage tank, and the device is restored to the initial state.

In an embodiment, in the purging 4), a purging time is controlled by the multiple total reflection infrared spectrum analyzer, if the amine concentration in the previous step is higher than the preset value, the purging time is prolonged, and washing 3) and purging with the inert gas 4) are repeated until the amine concentration of the waste liquid is lower than the preset value, and the device is restored to the initial state.

In an embodiment, in the pre-regenerating 5), if an amine concentration of the waste liquid flowing out of the bottom of the ion exchange bed recorded by the multiple total reflection infrared spectrum analyzer is higher than the preset value, a judgment value of the amine concentration for the multiple total reflection infrared spectrum analyzer in a washing step in a next purifying cycle is reduced, and the washing time and the purging time are prolonged.

In an embodiment, in the regenerating 6), if an amine concentration of the recycled lye flowing out of the bottom of the ion exchange bed recorded by the multiple total reflection infrared spectrum analyzer is higher than a preset value, an amount of the amine solution of the next cycle flowing into the ion exchange bed is increased according to a result of the third flow meter, a time of a subsequent purging with the inert gas is prolonged, a judgment value of the amine concentration for the multiple total reflection infrared spectrum analyzer in the washing step in the next purifying cycle is reduced, and the washing time and the purging time are prolonged.

BRIEF DESCRIPTION OF THE DRAWINGS

The drawings constituting a part of this specification are used to provide a further understanding of the present disclosure, and embodiments of the present disclosure are used to explain the present disclosure but do not limit the present disclosure, in which:

FIG. 1 is a schematic diagram showing a device for purifying an organic amine solution of the present disclosure.

REFERENCE NUMERALS

X1: ion exchange bed; D1: multiple total reflection infrared spectrum analyzer; C1: inert gas cylinder; F1 to F3: flow meters; P1 and P2: liquid adding pumps; T1 to T2: liquid storage tanks; V1 to V8: valves.

DETAILED DESCRIPTION

In order to better understand the present disclosure, the technical solutions in embodiments of the present disclosure will be described clearly with reference to the drawings in embodiments of the present disclosure. Embodiments described are only a part of embodiments, not all the embodiments of the present disclosure, and shall not be construed to limit the present disclosure. In addition, to prevent a concept of the present disclosure from being ambiguous, structures and technology of the known art will be omitted. All other embodiments obtained by those skilled in the art according to embodiments of the present disclosure without inventive efforts shall fall within the protection scope of the present disclosure.

The drawings show various schematic diagrams according to embodiments of the present disclosure, which are not drawn to scale, some details are enlarged and some details may be omitted for clarity of presentation. Shapes of various regions and layers shown in the drawings and relative size and positional relationship between them are only exemplary. In practice, there may be deviations due to manufacturing tolerances or technical limitations, and areas/layers with different shapes, sizes, and relative positions may be designed according to needs.

In context of the present disclosure, when a layer/element is referred to as being "above" another layer/element, the layer/element may be directly on the other layer/element, or there may be an intermediate layer/element between them. In addition, if a layer/element is located "above" another layer/element in one orientation, the layer/element may be located "below" the other layer/element in an opposite orientation.

It should be noted that the terms "first", "second" and the like in specification and in claims are used for distinguishing between similar elements and not necessarily for describing a sequential or chronological order. It should be understood that the terms used are interchangeable under appropriate circumstances and that it is possible to implement operations of embodiments of the present disclosure described herein in other sequences different from those described or illustrated in the present disclosure. In addition, the terms "including" and "having" and any variations of them are intended to cover non-exclusive inclusions. For example, a process, method, system, product, or device that includes a series of steps or units is not necessarily limited to those clearly listed steps or units, but may include other steps or units which are not clearly listed or are inherent to the process, method, product, or device.

The present disclosure provides a device and a method for purifying an organic amine solution. The present device may perform operations of the present method, that is, the method may be applied by the present device, and the device and the method have a low amine loss. The device and the method of the present disclosure are capable of solving the technical problem that a control program of an existing purification device is not flexible and cannot be adjusted according to a solution concentration and an operation state of the purification device.

The present disclosure is described in detail with reference to the drawings as follows.

As shown in FIG. 1, the present disclosure provides in an embodiment a device for purifying an organic amine solution, and the device has a low amine loss and includes an ion exchange bed X1. The ion exchange bed X1 has a top cover and a bottom cover, each provided with a filter screen. The ion exchange bed X1 is filled with an ion exchange resin, such as a cation exchange resin, an anion exchange resin or an anion-cation-mixing exchange resin. The filter screens connected to the top cover and the bottom cover may prevent the resin from flowing out of the ion exchange bed X1. The ion exchange bed X1 has an upper feeding port, through which the ion exchange bed X1 is communicated with an inert gas cylinder C1, a fifth liquid storage tank T5 and a second liquid adding pump P2 by pipelines. Gas contained in the inert gas cylinder C1 is an inert gas, such as nitrogen, argon or helium. A first flow meter F1 is provided on an outlet pipeline of the inert gas cylinder C1. A seventh valve V7 is provided on a discharging pipeline of the fifth liquid storage tank T5. A second flow meter F2 is provided on a discharging pipeline of the second liquid adding pump P2. The second liquid adding pump P2 has an extraction port, through which the second liquid adding pump P2 is communicated with a third liquid storage tank T3 and a sixth liquid storage tank T6 by pipelines. A sixth valve V6 is provided on a discharging pipeline of the third liquid storage tank T3, and an eighth valve V8 is provided on a discharging pipeline of the sixth liquid storage tank T6. The ion exchange bed X1 has a lower feeding port, through which the ion exchange bed X1 is communicated with a first liquid adding pump P1 by a pipeline. The first liquid adding pump P1 has an extraction port, through which the first liquid adding pump P1 is communicated with a first liquid storage tank T1 by a pipeline. A third flow meter F3 and a first valve V1 are provided on a discharging pipeline of the first liquid adding pump P1, respectively. The ion exchange bed X1 has a lower discharging port, through which the ion exchange bed X1 is communicated with a second liquid storage tank T2, a third liquid storage tank T3 and a fourth liquid storage tank T4 by pipelines. The ion exchange bed X1 has an upper discharging port, through which the ion exchange bed X1 is communicated with the fourth liquid storage tank T4 by a pipeline. A multiple total reflection infrared spectrum analyzer D1 is provided on a discharging pipeline from a lower end of the ion exchange bed X1. A detection window of the multiple total reflection infrared spectrum analyzer D1 is embedded into an outside wall of a bottom pipeline of the ion exchange bed X1, and a surface of the window is in a direct contact with a waste liquid to detect a concentration of the organic amine in a liquid flowing over/across the window. The detected result will determine a duration of each step in subsequent purification process and the number of times this step is performed. The infrared spectrum window of the multiple total reflection infrared spectrum analyzer D1 may have a material of single crystal silicon, zinc selenide, diamond or calcium fluoride. A third valve V3 is provided on a feeding pipeline of the second liquid storage tank T2, a fourth valve V4 is provided on a feeding pipeline of the third liquid storage tank T3, a fifth valve V5 is provided on a pipeline communicating the fourth liquid storage tank T4 the ion exchange bed X1 through the lower discharging port, and a second valve V2 is provided on a pipeline communicating the fourth liquid storage tank T4 with the ion exchange bed X1 through the upper discharging port.

As shown in FIG. 1, the first liquid storage tank T1 is a raw liquid tank, the second liquid storage tank T2 is a waste liquid tank, the third liquid storage tank T3 is a recycled lye tank, the fourth liquid storage tank T4 is a purified liquid tank, the fifth liquid storage tank T5 is a deionized water tank, and the sixth liquid storage tank T6 is a purified lye tank. A gas discharge port is provided at a top of the second liquid storage tank T2 and a top of the fourth liquid storage tank T4, respectively. The sixth liquid storage tank T6 contains alkaline solutions such as sodium hydroxide and potassium hydroxide for regenerating the ion exchange resin.

As shown in FIG. 1, an initial state of the device is that the values V1 to V8 and the flow meters F1 to F3 are closed, and the device is activated to perform the following steps in a cycle.

Step 1): purifying. The organic amine solution to be purified is placed in the first liquid storage tank T1, and the first liquid adding pump P1, the first valve V1 and the second valve V2 are opened to start the cycle. The amine solution is fed into the ion exchange bed X1 from a bottom thereof, and is purified. The purified solution is transported to the fourth liquid storage tank T4 from an upper end of the ion exchange bed X1, and the device is restored to the initial state after the purifying is performed for a period of time.

Step 2): purging with an inert gas. The inert gas cylinder C1, the first flow meter F1 and the fifth valve V5 are opened, the inert gas is introduced from the top of the ion exchange bed X1 to discharge the amine solution remaining in the ion exchange bed X1 into the fourth liquid storage tank T4, and the device is restored to the initial state.

Step 3): washing with water. The seventh valve V7 is opened to add deionized water contained in the fifth liquid storage tank T5 to the ion exchange bed X1 from the top thereof, and the seventh valve V7 is closed until a preset liquid level is reached. The third valve V3 is opened to discharge a waste liquid to the second liquid storage tank T2 after ion exchange resin in the ion exchange bed X1 is soaked with the deionized water for a preset period of time. If an amine concentration of the waste liquid (obtained from washing the ion exchange bed X1 with water) detected by the multiple total reflection infrared spectrum analyzer D1 is higher than a preset value, the third valve V3 is closed and the fifth valve V5 is opened to allow the waste liquid with a high amine concentration to flow into the fourth liquid storage tank T4. The device is restored to the initial state.

Step 4): purging with the inert gas. The inert gas cylinder C1 and the first flow meter F1 are opened, and the third valve V3 or the fifth valve V5 is opened according to a detected result of the multiple total reflection infrared spectrum analyzer D1. The inert gas is introduced from the top of the ion exchange bed X1 to discharge the waste liquid remaining in the ion exchange bed X1. If the amine concentration of the waste liquid in a previous step is lower than the preset value, the third valve V3 is opened to discharge the waste liquid into the second liquid storage tank T2, otherwise, the fifth valve V5 is opened to discharge the waste liquid into the liquid storage tank T4. A purging time is controlled by the multiple total reflection infrared spectrum analyzer D1. If the amine concentration in the previous step is higher than the preset value, the purging time is prolonged, and washing of step 3) and purging with the inert gas of step 4) are repeated until the amine concentration of the waste liquid is lower than the preset value, and the device is restored to the initial state.

Step 5): pre-regenerating. The second liquid adding pump P2, the sixth valve V6 and the third valve V3 are opened, a recycled lye contained in the third liquid storage tank T3 is added to the ion exchange bed X1 from the top thereof, to rinse the ion exchange resin from top to bottom for pre-regenerating. A generated waste liquid flows into the second liquid storage tank T2, and the device is restored to the initial state. If an amine concentration of the waste liquid flowing out of the bottom of the ion exchange bed X1 recorded by the multiple total reflection infrared spectrum analyzer D1 is relative high, a judgment value of the amine concentration detected by the multiple total reflection infrared spectrum analyzer D1 in a washing step of a next purifying cycle is reduced, and the washing time and the purging time are prolonged.

Step 6): regenerating. The second liquid adding pump P2, the eighth valve V8 and the fourth valve V4 are opened, a lye contained in the sixth storage tank T6 is added into the ion exchange bed X1 from the top thereof by the second liquid adding pump P2, to wash and remove impurity ions adsorbed on the resin surface from top to bottom to regenerate the resin. A washed waste liquid is collected to the third liquid storage tank T3 as the recycled lye, and the device is restored to the initial state. If an amine concentration of the recycled lye flowing out of the bottom of the ion exchange bed X1 recorded by the multiple total reflection infrared spectrum analyzer D1 is relative high, an amount of the amine solution of the next cycle flowing into the ion exchange bed X1 is increased (in this case a result of the third flow meter F3 is also considered), the time of subsequent purging with the inert gas is prolonged, the judgment value of the amine concentration detected by the multiple total reflection infrared spectrum analyzer D1 in the washing step of the next purifying cycle is reduced, and the washing time and the purging time are prolonged.

Step 7): purging with the inert gas. The inert gas cylinder C1, the first flow meter F1 and the third valve V3 are opened to discharge the lye remaining in the ion exchange bed X1 into the second liquid storage tank T2, and the device is restored to the initial state.

Step 8): completing the cycle and starting the next cycle.

In the device for purifying the organic amine solution, the concentration of the organic amine in the solution discharged from the ion exchange bed X1 may be detected by the multiple total reflection infrared spectrum analyzer D1 in real time, to allow an operator to control the valves to be open or closed according to a real-time detected result of the multiple total reflection infrared spectrum analyzer D1, thus solving problems in the art that an existing purification device applies a fixed operating program which is unable to respond to actual operating conditions in real time and thus operating parameters cannot be optimized. Furthermore, in the present disclosure, the valves V1-V7 may be electronically controlled valves. Detected results of the multiple total reflection infrared spectrum analyzer D1 can be input to a control device of the purification device, and thus it can automatically control each electronically controlled valve according to the detected concentration. Further, the present disclosure may combine a function of amine concentration measurement and a function of autonomous adjustment of the operation program of the device, and may acquire information of an amine loss during the operations of the device. Therefore, in the present disclosure, the operating parameters can be optimized to reduce the amine loss and thus operating costs can be reduced.

EXAMPLE 1

An II-type anion exchange resin is placed in an ion exchange bed X1, and a detection window of the multiple total reflection infrared spectrum analyzer D1 is a silicon window, which has a number of reflections of 20. An inert gas cylinder C1 is a nitrogen cylinder. A liquid storage tank T1 is filled with a 30 wt % methyldiethanolamine solution to be purified, and a liquid storage tank T6 is filled with a 5 wt % potassium hydroxide aqueous solution.

The device is activate to perform the following steps.

Step 1): purifying. The organic amine solution to be purified is placed in the first liquid storage tank T1, and a first liquid adding pump P1, a first valve V1 and a second valve V2 are opened to start the cycle. The amine solution is fed into the ion exchange bed X1 from a bottom thereof, and is purified. The purified solution is transported to a fourth liquid storage tank T4 from an upper end of the ion exchange bed X1. A linear speed of the methyldiethanolamine solution flowing across a surface of the resin is 1 cm/min. The purifying is performed for 0.5 h. The device is restored to the initial state.

Step 2): purging with an inert gas. The inert gas cylinder C1, a first flow meter F1 and a fifth valve V5 are opened, the inert gas is introduced from the top of the ion exchange bed X1 to discharge the amine solution remaining in the ion exchange bed X1 into the fourth liquid storage tank T4, and the device is restored to the initial state. A default value of a purging time is 2 min.

Step 3): washing with water. A seventh valve V7 is opened to add deionized water contained in a fifth liquid storage tank T5 to the ion exchange bed X1 from the top of the ion exchange bed X1, and the seventh valve V7 is closed until a preset liquid level is reached. A third valve V3 is opened to discharge a waste liquid to a second liquid storage tank T2 after the ion exchange resin in the ion exchange bed X1 is soaked with the deionized water for a preset period of time. If an amine concentration of the waste liquid (obtained from washing the ion exchange bed X1 with water) detected by the multiple total reflection infrared spectrum analyzer D1 is higher than 3 wt %, the third valve V3 is closed and the fifth valve V5 is opened to allow the waste liquid with a high amine concentration to flow into the fourth liquid storage tank T4. The device is restored to the initial state.

Step 4): purging with the inert gas. The inert gas cylinder C1 and the first flow meter F1 are opened, and the third valve V3 or the fifth valve V5 is opened according to a detected result of the multiple total reflection infrared spectrum analyzer D1. The inert gas is introduced from the top of the ion exchange bed X1 to discharge the waste liquid remaining in the ion exchange bed X1. If the amine concentration of the waste liquid in the previous step is lower than 3 wt %, the third valve V3 is opened to discharge the waste liquid into the second liquid storage tank T2, otherwise, the fifth valve V5 is opened to discharge the waste liquid into the liquid storage tank T4. The purging time is controlled by the multiple total reflection infrared spectrum analyzer D1. If the amine concentration in the previous step is higher than 3 wt %, the purging time is prolonged, and washing of step 3) and purging with the inert gas of step 4) are repeated until the amine concentration of the waste liquid is lower than the preset value, and the device is restored to the initial state.

Step 5): pre-regenerating. A second liquid adding pump P2, a sixth valve V6 and the third valve V3 are opened, a recycled lye contained in the third liquid storage tank T3 is added to the ion exchange bed X1 from the top thereof, to rinse the ion exchange resin from top to bottom for pre-regenerating. A generated waste liquid flows into the second liquid storage tank T2, and the device is restored to the initial state. If an amine concentration of the waste liquid flowing out of the bottom of the ion exchange bed X1 recorded by the multiple total reflection infrared spectrum analyzer D1 is higher than 3 wt %, a judgment value of the amine concentration for the multiple total reflection infrared spectrum analyzer D1 in a washing step in a next purifying cycle is reduced to 2% by weight, and the washing time and the purging time are prolonged as 2 times of their default values.

Step 6): regenerating. The second liquid adding pump P2, an eighth valve V8 and a fourth valve V4 are opened, a lye contained in the sixth storage tank T6 is added to the ion exchange bed X1 from the top thereof by the second liquid adding pump P2, to wash and remove impurity ions adsorbed on the resin surface from top to bottom to regenerate the resin. A washed waste liquid is collected to the third liquid storage tank T3 as the recycled lye, and the device is restored to the initial state. If an amine concentration of the recycled lye flowing out of the bottom of the ion exchange bed X1 recorded by the multiple total reflection infrared spectrum analyzer D1 is higher than the preset value, an amount of the amine solution of the next cycle flowing into the ion exchange bed X1 is increased to be 1.5 times of the amount of the amine solution of the current cycle (in this case a result of the third flow meter F3 is also considered), the time of subsequent purging with the inert gas is prolonged to be 2 times of the default value, a judgment value of the amine concentration for the multiple total reflection infrared spectrum analyzer D1 in the washing step in the next purifying cycle is reduced to 2% by weight, and the washing time and the purging time are prolonged to be 2 times of their default values.

Step 7): purging with inert gas. The inert gas cylinder C1, the first flow meter F1 and the third valve V3 are opened to discharge the lye remaining in the ion exchange bed X1 into the second liquid storage tank T2, and the device is restored to the initial state.

Step 8): completing the cycle and starting the next cycle.

If the washing time and the purging time are modified in the steps 5) and 6) in three consecutive cycles, default times of the two steps are increased by 1 time. If the default time is increased by more than 5 times after a number of cycles, an operator will be informed of overhaul and maintenance of the device.

EXAMPLE 2

An anion-cation exchange resin is placed in an ion exchange bed X1, and a detection window of the multiple total reflection infrared spectrum analyzer D1 is a zinc selenide window, which has a number of reflections of 25. An inert gas cylinder C1 is a nitrogen cylinder. A liquid storage tank T1 is filled with a 35 wt % monoethanolamine solution to be purified, and a liquid storage tank T6 is filled with a 5 wt % sodium hydroxide aqueous solution.

The device is activate to perform the following steps.

Step 1): purifying. The monoethanolamine solution to be purified is placed in the first liquid storage tank T1, and a first liquid adding pump P1, a first valve V1 and a second valve V2 are opened to start the cycle. The amine solution is fed into the ion exchange bed X1 from a bottom thereof, and is purified, and the purified solution is transported to a fourth liquid storage tank T4 from the top of the ion exchange bed X1. A linear speed of the monoethanolamine solution flowing across a surface of the resin is 0.5 cm/min. The purifying is performed for 50 min. The device is restored to the initial state.

Step 2): purging with an inert gas. The inert gas cylinder C1, a first flow meter F1 and a fifth valve V5 are opened, the inert gas is introduced from the top of the ion exchange bed X1 to discharge the monoethanolamine solution remaining in the ion exchange bed X1 into the fourth liquid storage tank T4, and the device is restored to the initial state. A default value of a purging time is 2 min.

Step 3): washing with water. A seventh valve V7 is opened to add deionized water contained in a fifth liquid storage tank T5 to the ion exchange bed X1 from the top of the ion exchange bed X1, and the seventh valve V7 is closed until a preset liquid level is reached. A third valve V3 is opened to discharge a waste liquid to a second liquid storage tank T2 after the ion exchange resin in the ion exchange bed X1 is soaked with the deionized water for a preset period of time. If a monoethanolamine concentration of the waste liquid (obtained from washing the ion exchange bed X1 with water) detected by the multiple total reflection infrared spectrum analyzer D1 is higher than 3 wt %, the third valve V3 is closed and the fifth valve V5 is opened to allow the waste liquid with a high amine concentration to flow into the fourth liquid storage tank T4. The device is restored to the initial state.

Step 4): purging with the inert gas. The inert gas cylinder C1 and the first flow meter F1 are opened, and the third valve V3 or the fifth valve V5 is opened according to a detected result of the multiple total reflection infrared spectrum analyzer D1. The inert gas is introduced from the top of the ion exchange bed X1 to discharge the waste liquid remaining in the ion exchange bed X1. If the monoethanolamine concentration of the waste liquid in the previous step is lower than 3 wt %, the third valve V3 is opened to discharge the waste liquid into the second liquid storage tank T2, otherwise, the fifth valve V5 is opened to discharge the waste liquid into the liquid storage tank T4. The purging time is controlled by the multiple total reflection infrared spectrum analyzer D1. If the monoethanolamine concentration in the previous step is higher than 3 wt %, the purging time is prolonged, and washing of step 3) and purging with the inert gas of step 4) are repeated until the amine concentration of the waste liquid is lower than the preset value 3 wt %, and the device is restored to the initial state.

Step 5): pre-regenerating. A second liquid adding pump P2, a sixth valve V6 and the third valve V3 are opened, a recycled lye contained in the third liquid storage tank T3 is added to the ion exchange bed X1 from the top thereof, to rinse the ion exchange resin from top to bottom for pre-regenerating. A generated waste liquid flows into the second liquid storage tank T2, and the device is restored to the initial state. If a monoethanolamine concentration of the waste liquid flowing out of the bottom of the ion exchange bed X1 recorded by the multiple total reflection infrared spectrum analyzer D1 is higher than 3 wt %, a judgment value of the monoethanolamine concentration for the multiple total reflection infrared spectrum analyzer D1 in a washing step in a next purifying cycle is reduced to 2% by weight, and the washing time and the purging time are prolonged as 2 times of their default values.

Step 6): regenerating. The second liquid adding pump P2, an eighth valve V8 and a fourth valve V4 are opened, a lye contained in the sixth storage tank T6 is added to the ion exchange bed X1 from the top thereof by the second liquid adding pump P2, to wash and remove impurity ions adsorbed on the resin surface from top to bottom to regenerate the resin. A washed waste liquid is collected to the third liquid storage tank T3 as the recycled lye, and the device is restored to the initial state. If a monoethanolamine concentration of the recycled lye flowing out of the bottom of the ion exchange bed X1 recorded by the multiple total reflection infrared spectrum analyzer D1 is higher than the preset value, an amount of the amine solution of the next cycle flowing into the ion exchange bed X1 is increased to be 1.5 times of the amount of the amine solution of the current cycle (in this case a result of the third flow meter F3 is also considered), the time of subsequent purging with the inert gas is prolonged to be 2 times of the default value, a judgment value of the amine concentration for the multiple total reflection infrared spectrum analyzer D1 in the washing step in the next purifying cycle is reduced to 2% by weight, and the washing time and the purging time are prolonged to be 2 times of their default values.

Step 7): purging with the inert gas. The inert gas cylinder C1, the first flow meter F1 and the third valve V3 are opened to discharge the lye remaining in the ion exchange bed X1 into the second liquid storage tank T2, and the device is restored to the initial state.

Step 8): completing the cycle and starting the next cycle.

The above descriptions are only examples of the present disclosure and are not intended to limit, and any changes may be made on a basis of the technical solutions according to the technical ideas proposed in the present disclosure, should be included in the protection scope of the claims of this invention.

What is claimed is:

1. A device for purifying an organic amine solution, comprising an ion exchange bed (X1),
   wherein the ion exchange bed (X1) has an upper feeding port, through which the ion exchange bed (X1) is communicated with an inert gas cylinder (C1), a fifth liquid storage tank (T5) and a second liquid adding pump (P2) by pipelines, a first flow meter (F1) is provided on an outlet pipeline of the inert gas cylinder (C1), and a seventh valve (V7) is provided on a discharging pipeline of the fifth liquid storage tank (T5);
   wherein the ion exchange bed (X1) has a lower feeding port, through which the ion exchange bed (X1) is communicated with a first liquid adding pump (P1) by a pipeline, and the first liquid adding pump (P1) has an extraction port, through which the first liquid adding pump (P1) is communicated with a first liquid storage tank (T1) by a pipeline;
   wherein the ion exchange bed (X1) has a lower discharging port, through which the ion exchange bed (X1) is communicated with a second liquid storage tank (T2), a third liquid storage tank (T3) and a fourth liquid storage tank (T4) by pipelines, a multiple total reflection infrared spectrum analyzer (D1) is provided on a discharging pipeline from a lower end of the ion exchange bed (X1), a third valve (V3) is provided on a feeding pipeline of the second liquid storage tank (T2), a fourth valve (V4) is provided on a feeding pipeline of the third liquid storage tank (T3), and a fifth valve (V5) is provided on a pipeline communicating the fourth liquid storage tank (T4) with the ion exchange bed (X1) through the lower discharging port; and
   wherein the ion exchange bed (X1) has an upper discharging port, through which the ion exchange bed (X1) is communicated with the fourth liquid storage tank (T4) by a pipeline, and a second valve (V2) is provided on a pipeline communicating the fourth liquid storage tank (T4) with the ion exchange bed (X1) through the upper discharging port.

2. The device according to claim 1, wherein a second flow meter (F2) is provided on a discharging pipeline of the second liquid adding pump (P2), and the second liquid adding pump (P2) has an extraction port, through which the second liquid adding pump (P2) is communicated with the third liquid storage tank (T3) and a sixth liquid storage tank (T6) by pipelines.

3. The device according to claim 2, wherein a sixth valve (V6) is provided on a discharging pipeline of the third liquid storage tank (T3), and an eighth valve (V8) is provided on a discharging pipeline of the sixth liquid storage tank (T6).

4. The device according to claim 1, wherein a third flow meter (F3) and a first valve (V1) are provided on a discharging pipeline of the first liquid adding pump (P1).

5. The device according to claim 1, wherein the first liquid storage tank (T1) is a raw liquid tank, the second liquid storage tank (T2) is a waste liquid tank, the third liquid storage tank (T3) is a recycled lye tank, the fourth liquid storage tank (T4) is a purified liquid tank, and the fifth liquid storage tank (T5) is a deionized water tank.

6. The device according to claim 2, wherein the sixth liquid storage tank (T6) is a purified lye tank.

7. The device according to claim 1, wherein a gas discharge port is provided at a top of the second liquid storage tank (T2) and a top of the fourth liquid storage tank (T4), respectively.

8. A method for purifying an organic amine solution, performed by the device according to claim 1, the method comprising:
   1): purifying: placing the organic amine solution to be purified in the first liquid storage tank (T1), starting a cycle, opening the first liquid adding pump (P1), a first valve (V1) and the second valve (V2), feeding the amine solution into the ion exchange bed (X1) from a bottom of the ion exchange bed (X1), purifying the amine solution, transporting a purified solution to the fourth liquid storage tank (T4) from a top of the ion exchange bed (X1), and restoring the device to an initial state after the purifying is performed for a period of time;

2): purging with an inert gas: opening the inert gas cylinder (C1), the first flow meter (F1) and the fifth valve (V5), introducing the inert gas into the ion exchange bed (X1) from the top of the ion exchange bed (X1) to discharge the amine solution remaining in the ion exchange bed (X1) into the fourth liquid storage tank (T4), and restoring the device to the initial state;

3): washing with water: opening the seventh valve (V7) to add deionized water contained in the fifth liquid storage tank (T5) to the ion exchange bed (X1) from the top of the ion exchange bed (X1), closing the seventh valve (V7) until a preset liquid level is reached, and opening the third valve (V3) to discharge a waste liquid to the second liquid storage tank (T2) after the ion exchange resin in the ion exchange bed (X1) is soaked with the deionized water for a preset period of time;

4): purging with the inert gas: opening the inert gas cylinder (C1) and the first flow meter (F1), opening the third valve (V3) or the fifth valve (V5) according to a detected result of the multiple total reflection infrared spectrum analyzer (D1), introducing the inert gas from the top of the ion exchange bed (X1) to discharge the waste liquid remaining in the ion exchange bed (X1), if an amine concentration of the waste liquid in a previous step is lower than a preset value, opening the third valve (V3) to discharge the waste liquid into the second liquid storage tank (T2), otherwise, opening the fifth valve (V5) to discharge the waste liquid into the fourth liquid storage tank (T4);

5): pre-regenerating: opening the second liquid adding pump (P2), a sixth valve (V6) and the third valve (V3), adding a recycled lye contained in the third liquid storage tank (T3) to the ion exchange bed (X1) from the top of the ion exchange bed (X1), rinsing the ion exchange resin from top to bottom for pre-regenerating, transporting the generated liquid into the second liquid storage tank (T2), and restoring the device to the initial state;

6): regenerating: opening the second liquid adding pump (P2), an eighth valve (V8) and the fourth valve (V4), adding a lye contained in a sixth liquid storage tank (T6) to the ion exchange bed (X1) from the top of the ion exchange bed (X1) by the second liquid adding pump (P2), and washing and removing impurity ions adsorbed on the resin surface from top to bottom to regenerate the resin, collecting the washed waste liquid to the third liquid storage tank (T3) as the recycled lye, and restoring the device to the initial state;

7): purging with the inert gas: opening the inert gas cylinder (C1), the first flow meter (F1) and the third valve (V3) to discharge the lye remaining in the ion exchange bed (X1) into the second liquid storage tank (T2), and restoring the device to the initial state; and 8): completing the cycle and starting a next cycle.

9. The method according to claim 8, wherein in the washing 3), if the amine concentration of the waste liquid detected by the multiple total reflection infrared spectrum analyzer (D1) is higher than the preset value, the third valve (V3) is closed and the fifth valve (V5) is opened to allow the waste liquid with a high amine concentration flow into the fourth liquid storage tank (T4), and the device is restored to the initial state.

10. The method according to claim 8, wherein in the purging 4), a purging time is controlled by the multiple total reflection infrared spectrum analyzer (D1), if the amine concentration in the previous step is higher than the preset value, the purging time is prolonged, and washing 3) and purging with the inert gas 4) are repeated until the amine concentration of the waste liquid is lower than the preset value, and the device is restored to the initial state.

11. The method according to claim 8, wherein in the pre-regenerating 5), if an amine concentration of the waste liquid flowing out of the bottom of the ion exchange bed (X1) recorded by the multiple total reflection infrared spectrum analyzer (D1) is higher than the preset value, a judgment value of the amine concentration for the multiple total reflection infrared spectrum analyzer (D1) in a washing step in a next purifying cycle is reduced, and the washing time and the purging time are prolonged.

12. The method according to claim 8, wherein in the regenerating 6), if an amine concentration of the recycled lye flowing out of the bottom of the ion exchange bed (X1) recorded by the multiple total reflection infrared spectrum analyzer (D1) is higher than a preset value, an amount of the amine solution of the next cycle flowing into the ion exchange bed (X1) is increased according to a result of a third flow meter (F3), a time of a subsequent purging with the inert gas is prolonged, a judgment value of the amine concentration for the multiple total reflection infrared spectrum analyzer (D1) in the washing step in the next purifying cycle is reduced, and the washing time and the purging time are prolonged.

* * * * *